United States Patent [19]

Cantekin

[11] 4,168,697
[45] Sep. 25, 1979

[54] MIDDLE EAR VENTILATING TUBE AND METHOD

[76] Inventor: Erdem I. Cantekin, 5321½ Wilkins Ave., Pittsburgh, Pa. 15217

[21] Appl. No.: 862,841

[22] Filed: Dec. 21, 1977

Related U.S. Application Data

[63] Continuation of Ser. No. 759,677, Jan. 17, 1977, which is a continuation of Ser. No. 598,681, Jul. 24, 1975.

[51] Int. Cl.² .......................... A61B 19/00; A61F 1/18
[52] U.S. Cl. .................................... 128/1 R; 128/151; 128/350 R; 3/1
[58] Field of Search .................. 128/1 R, 350 R, 151, 128/152; 55/16; 3/1

[56] References Cited

U.S. PATENT DOCUMENTS

| | | | |
|---|---|---|---|
| 3,228,394 | 1/1966 | Ayres | 128/142 |
| 3,530,860 | 9/1970 | Majoros | 128/350 R X |
| 3,807,409 | 4/1974 | Paparella et al. | 128/350 R |
| 3,916,873 | 11/1975 | Wasserman | 128/1 R |

Primary Examiner—Dalton L. Truluck
Attorney, Agent, or Firm—Buell, Blenko & Ziesenheim

[57] ABSTRACT

A ventilating tube and method are provided for maintaining a desired gaseous partial pressure in the middle ear comprising in combination a tube having an axial lumen, means on the tube holding the tube in place in a wall of the inner ear and a selective permeability membrane closing the tube lumen.

7 Claims, 5 Drawing Figures

MIDDLE EAR VENTILATING TUBE AND METHOD

This application is a continuation of my copending application Ser. No. 759,677, filed Jan. 17, 1977 which in turn was a continuation of Ser. No. 598,681, filed July 24, 1975.

This invention relates to middle ear ventilating tubes and methods and particularly a membrane ventilating tube for the middle ear.

In the early part of the nineteenth century, Eustachian tube malfunction was suggested as a cause of middle ear effusion and myringotomy was performed in an effort to cure the disease. Different methods were attempted to keep the hole open following myringotomy. In the 1860's Politzer introduced his hard rubber eyelet middle ear ventilation tube. In the 1950's, almost a century later, the ventilation tube was rediscovered when Armstrong reported a vinyl tube for the ventilation of the middle ear; Armstrong, B. W.: a New Treatment of Chronic Secretory Otitis Media., *Archives of Otolaryngology*, 59:653–654, 1954. Since then a variety of new tubes have been introduced with the basic principle and design of the original Politzer eyelet. Typical of the more recent ventilating tube is that disclosed by M. M. Paparella et al. in U.S. Pat. No. 3,807,409, issued Apr. 30, 1974.

The relationship between otitis media and poor Eustachian tube function is not totally proven but there appears to be some evidence that when the intermittent opening of Eustachian tube is impaired the middle ear cavity behaves like an unventilated gas pocket. The gases tend to equilibrate with the blood-tissue environment resulting in subatmospheric middle ear pressures.

The purpose of the tympanostomy or ventilating tube is to substitute for Eustachian tube function by ventilating, protecting and draining the middle ear cavity. Then, the ideal prosthesis should behave in a similar manner as the Eustachian tube functions for the typanum. However, introduction of a conventional tympanostomy tube into the tympanic membrane changes the physiology of the middle ear-Eustachian tube-nasopharynx system. The tympanum is converted in an open cavity instead of a closed-ventilated cavity. The present tube appears to perform the ventilation and drainage functions of the Eustachian tube but does not *protect* the middle ear. Persistent or recurrent bouts of otorrhea remains a troublesome complication due to exposure of middle ear cavity to the external canal or due to reflux or nasopharyngeal secretions into the tympanum. Also, post-insertion of the tube, curtailment of swimming and extra precaution during bathing is necessary since the patient must not get water in the ear.

If the disease is caused by the inadequate ventilation of the tympanum, a gas ventilating tube should perform in a similar manner as the natural tube. Unfortunately, there has been to date no ventilating tube which would perform this function adequately.

In normal Eustachian tube function, the gases absorbed in the middle cavity are replenished by a bolus of air entering the tympanum during intermittent opening of the Eustachian tube. Diffusion of gases through the tympanic membrane contributes a negligible amount of this gas renewal process. In other words, the gas tensions in the cavity are exclusively dependent on Eustachian tube ventilatory rate.

I have developed a ventilating tube which solves these problems. I provide a ventilating or myringotomy tube made up of a tube, an inner circular flange on the tube, an outer circular flange on the tube, said inner and outer flanges being spaced apart a distance sufficient to span the wall thickness of a tissue defining the area to be drained, said tube and flanges being made of pliable material compatible with body tissue and a biocompatible selective permeability membrane covering the outer end of the tube. Preferably the tube is made of a soft, resilient material such as polyethylene, silicone elastomer or any of the other materials historically used for ventilating tubes. The biocompatible selective permeability membrane must be one that is selectively permeable to oxygen in particular and may be any of the membranes used in membrane blood oxygenators such as silicone-polycarbonate copolymer, dimethyl silicone rubber, silicone elastomers such as Dow Cornings Silastic and General Electric's MEM-213 or any other equivalent selective permeability membrane material. The ventilator tube may have the shape shown in Paparella et al. U.S. Pat. No. 3,807,409 or any of the other well known shapes described by Armstrong (supra) and others.

In the foregoing general description of this invention I have set out certain objects, purposes and advantages of this invention. Other objects, purposes and advantages will be apparent from a consideration of the following discussion and the accompanying drawings in which.

Figure 1:
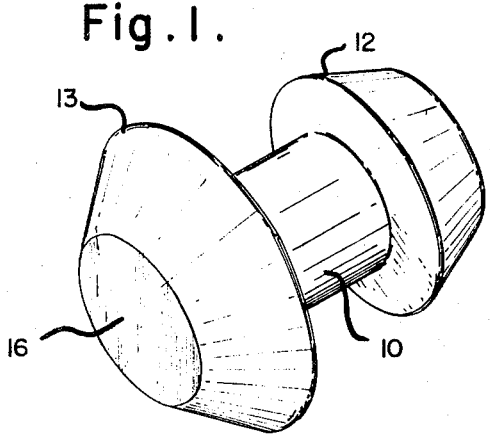
FIG. 1 is an isometric view of a ventilating or myringotomy tube according to this invention.
Figure 2:
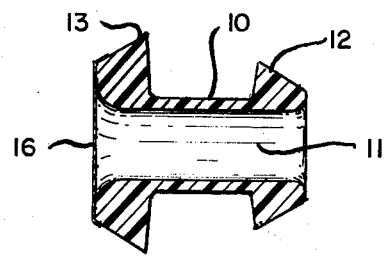
FIG. 2 is a section through the tube of FIG. 1.
Figure 4:
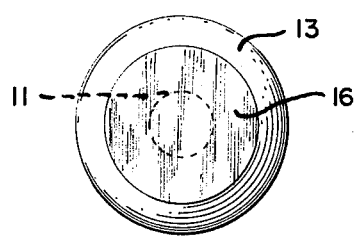
FIG. 4 is an end elevational view of the outer end of the tube of FIG. 1 viewed from the left.
Figure 3:
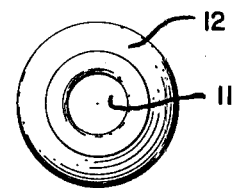
FIG. 3 is an end elevational view of the inner end of the tube of FIG. 1 viewed from the right.
Figure 5:
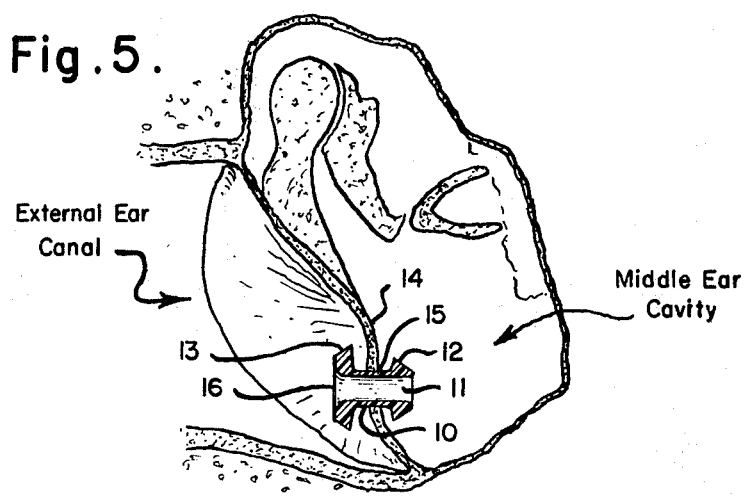
FIG. 5 is a section of the middle ear showing the ventilating tube of this invention in place.

Referring to the drawings I have illustrated a main tube 10 having an axial passage 11 therethrough. An inner flange 12 is fixed on the tube 10 at right angles to its axis forming a first radial ring. An outer flange 13 is fixed on the tube 10 at right angles to its axis forming a second radial ring spaced from the first ring a distance sufficient to span the wall thickness of the tympanic membrane 14 through which it is inserted by means of a small opening 15. The outer end of passage 11 is covered by a selective permeability membrane 16 such as silicone-polycarbonate copolymer.

This invention can perhaps be best understood by reference to the following examples of the use of tubes of this invention in patients afflicted with Eustachian tube malfunction.

One millimeter lumen diameter flanged tympanostomy tubes were prepared. A 1.5 min. diameter membrane cover of General Electric's permselective membrane MEM-213 which is a silicone rubber with 1/10 mil and ½ mil thickness was used as the selective permeability membrane. It was assumed that with a middle ear oxygen partial pressure of 83, the tube and 1/10 mil membrane can supply $0.615 \times 10^{-3}$ cc. of $O_2$/Min into the tympanum.

The prototype tubes were made by attaching a MEM-213 membrane on one end of a biflanged polyethylene tube. The membrane was secured to the outer flange of the tube by partially dissolving it with methylene chloride. Each tube was inspected under the operating microscope for possible pinholes and to determine the adequacy of the seal around the tubal flange. They were sterilized by Electron Beam radiation (Dose $2\times10^6$ Rads). Two different membrane thicknesses (1/10 mil and ½ mil) were used.

The efficacy of the membrane tubes was studied in a pilot project in 20 patients whose ages ranged from eight months to 56 years. They were candidates for bilateral myringotomy and tympanostomy tube insertion. Under general anesthesia following a conventional myringotomy incision in the anterior-superior quadrant of the tympanic membrane, the membrane tube was inserted by holding the stem part of the myringotomy tube with a curved forceps so as not to damage the membrane. In each case, a conventional ventilating tube was inserted in the contralateral tympanic membrane. The membrane thickness and the side of insertion were randomly selected. Eleven of the patients received ½ mil thick membrane tubes and none of them received 1/10 mil thick membrane tubes. In 15 cases, the tympanic membrane and middle ear appeared normal by pneumatic otoscopy. Tympanometry was performed in some and revealed intact tympanic membrane patterns with normal middle ear pressures, which verified that the membrane tube provided a complete seal and adequate ventilation for the middle ear. One patient failed to return for follow-up. In four cases, the membrane or the entire tube was extruded. Extrusion was attributed to improper surgical technique or faulty application of the membrane seal to the outer flange of the prototype tubes or persistent hydrostatic effusion pressure following insertion.

An interesting case was patient number 3, in whom the contralateral ear with the conventional ventilation tube had three bouts of otorrhea during the eleven month follow-up period, while the other ear with the membrane tube remained totally normal. The adequacy of the gas transport rate through the membrane was verified in case number 18. This patient had a small, dry chronic perforation of the tympanic membrane. Eustachian tube function studies on several occasions revealed Eustachian tube obstruction to air flow. A roentgenographic Eustachian tube study employing contrast media showed obstruction to liquid flow in both directions (retrograde and prograde). A membrane tube was inserted through the existing perforation of the tympanic membrane. At each follow-up visit during the next four months, pneumatic otoscopy and tympanometry showed an intact tympanic membrane and normal middle ear pressures. This patient maintained a normal tympanic membrane mobility and middle ear pressure during periodic visits showing that the membrane tube could supply enough air to tympanum without Eustachian tube ventilation.

As pointed out above two thicknesses of membrane tubes were used. The 1/10 mil thickness membrane tube had a capacity to ventilate the middle ear cavity without the aid of the Eustachian tube ventilation. The transport rates though the membrane were larger than the gas absorption rates. The ½ mil thick membrane tube had transport rates about five times less than the 1/10 mil membrane tube. However, it too produced satisfactory results although theoretically it is border-line. The reasons for that might be some overlooked aspects of gas diffusion in the middle ear process, possibility of very small gas leakage around the membrane seal over the tube, some infrequent ventilation of the middle ear cavity by the Eustachian tube and the possibility of facilitated transport through the membrane. In vivo, the movement of tympanic membrane with the contractions of tensor tympani muscle and the opening of the Eustachian tube may generate air flow currents in the middle ear. This air circulation may enhance the diffusion process through the membrane by the introduction of convective currents due to the velocity field. However, the ½ mil thickness membrane was successful in in vivo tests for whatever the reason and the device successfully maintained atmospheric pressures in the tympanum, compensated for Eustachian tube malfunction, prevented otorrhea and recurrence of middle ear effusions.

Although the theoretical solution for this complex biomedical problem has not been resolved, a trial prototype device with two different membrane thicknesses and gas transport capacitites was successful.

For permanent implants, a double-lumen tube might be used where the outer stem is made of a perforated material for tissue growth into inter-lumenal space. This tube would be held by tympanic membrane epithelial growth and the solid wall of the inner-lumen would maintain an open orifice. Such a tube could be implanted permanently in patients with blockage of the Eustachian tube. A modification on the same ventilation principle may be used for tympanic membrane reconstruction. A semi-permeable membrane stretched over an inert ring will have an independent ventilating mechanism. Such a self-ventilating artificial tympanic membrane will not suffer from the consequences of malfunction of the Eustachian tube.

While I have set out certain preferred practices and embodiments of my invention in the foregoing specification it will be understood that this invention may be otherwise embodied within the scope of the following claims.

I claim:

1. A ventilating tube for the middle ear comprising in combination a tube having an axial lumen, an inner circular flange secured to said tube, an outer circular flanges secured to said tube, said inner and outer flanges being substantially parallel and spaced apart a distance sufficient to span the wall thickness of a tissue defining the area to be ventilated, and a biocompatable membrane selectively permeable to gases, particularly oxygen and comparable in permeability to membranes used in membrane blood oxygenators and adapted to maintain a normal middle ear pressure and a substantial partial pressure of oxygen within the inner ear, closing the tube lumen.

2. A ventilating tube as claimed in claim 1 wherein the selective permeability member is selected to maintain a desired (gas) partial pressure in the middle ear.

3. A ventilating tube as claimed in claim 1 wherein the selective permeability membrane is selected from the group consisting of silicone-polycarbonate copolymer, dimethyl silicone rubber and silicone elastomers.

4. A ventilating tube as claimed in claim 1 wherein the selective permeability membrane is attached to the outer flange.

5. A ventilating tube as claimed in claim 1 wherein the tube and flanges are made from a material selected from the group silicone elastomers and polyethylene.

6. A ventilating tube as claimed in claim 1 wherein the selective permeability membrane covers the tube end adjacent the outer flange.

7. A ventilating tube as claimed in claim 1 wherein the selective permeability member is selected to maintain a desired oxygen partial pressure in the middle ear.

* * * * *

UNITED STATES PATENT AND TRADEMARK OFFICE
CERTIFICATE OF CORRECTION

PATENT NO. : 4,168,697
DATED : September 25, 1979
INVENTOR(S) : ERDEM I. CANTEKIN It is certified that error appears in the above-identified patent and that said Letters Patent are hereby corrected as shown below:

Column 1, line 52, the first word "or" should read --of--.

Signed and Sealed this

Eleventh Day of December 1979

[SEAL]

Attest:

SIDNEY A. DIAMOND

Attesting Officer

Commissioner of Patents and Trademarks